Figure 1:
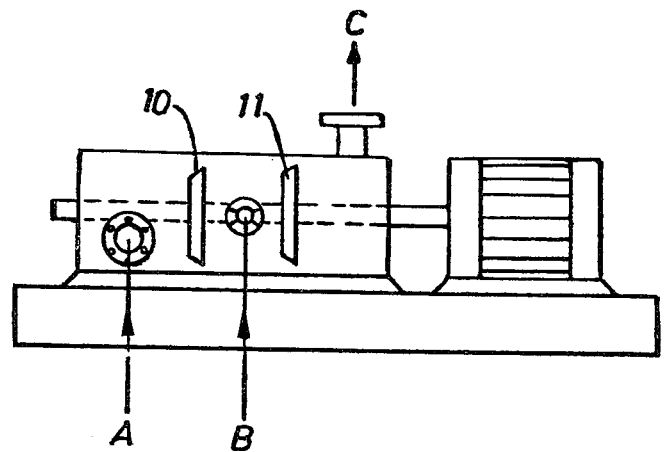

United States Patent [19]
Mitrowsky et al.

[11] 3,947,484
[45] Mar. 30, 1976

[54] CONTINUOUS PREPHOSGENATION PROCESS FOR THE PRODUCTION OF ORGANIC ISOCYANATES

[75] Inventors: Alexander Mitrowsky, Dormagen-Hakenbroich; Helmut Klappert, Cologne, both of Germany; Karl-Friedrich Zenner, Antwerp, Belgium; Wilhelm Hagen, Leverkusen, Germany

[73] Assignee: Bayer Aktiengesellschaft, Leverkusen, Germany

[22] Filed: May 31, 1974

[21] Appl. No.: 475,239

Related U.S. Application Data

[63] Continuation of Ser. No. 299,977, Oct. 24, 1972, abandoned.

[30] Foreign Application Priority Data
Oct. 26, 1971  Germany............................ 2153268

[52] U.S. Cl............................. 260/453 PH; 23/284
[51] Int. Cl.$^2$...................................... C07C 118/02
[58] Field of Search............................ 260/453 PH

[56] References Cited
UNITED STATES PATENTS

| | | | |
|---|---|---|---|
| 3,188,337 | 6/1965 | Gemassmer......................... | 260/453 |
| 3,321,283 | 5/1967 | Ewald .............................. | 260/453 X |
| 3,507,626 | 4/1970 | Horn................................ | 260/453 X |
| 3,781,320 | 12/1973 | Irwin................................. | 260/453 |

Primary Examiner—Lewis Gotts
Assistant Examiner—Dolph H. Torrence
Attorney, Agent, or Firm—Gene Harsh

[57] ABSTRACT

A process for pre-phosgenating organic primary amines is provided wherein a phosgene solution and an amine solution are combined in the suction side of a multiple stage rotary pump.

5 Claims, 2 Drawing Figures

CONTINUOUS PREPHOSGENATION PROCESS FOR THE PRODUCTION OF ORGANIC ISOCYANATES

This is a continuation, of application Ser. No. 299,977, filed Oct. 24, 1972, now abandoned.

Considerable difficulties are often involved in continuously carrying out industrial-scale chemical reactions due to blockages that occur when two or more reactants are combined in liquid, dissolved, suspended and/or gaseous form and reacted to form a solid end product or an intermediate product.

Reactions of the type that are prone to blockage include, for example, the continuous production of organic isocyanates by the reaction of amines with phosgene in the presence of organic solvents. Accordingly, the production cycle is divided into two separate process stages. In the first so-called "pre-phosgenation" or "cold-phosgenation" stage as described, for example, by W. Siefken, *Liebigs Annalen der Chemie* 562 (1949) page 96 the base solution, a suspension of the base or its carbonation product, is reacted with phosgene or with a solution of phosgene in an inert solvent, resulting in the formation of a suspension consisting of carbamic acid chloride, amine hydrochloride and small quantities of free isocyanate. In a second stage, the so-called "hot phosgenation" stage (see W. Siefken, supra), phosgene is introduced at an elevated temperature until the reaction forming the isocyanate has ceased. 2,4-tolylene diamine (I) is believed to undergo the following reaction:

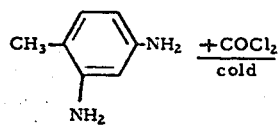

I

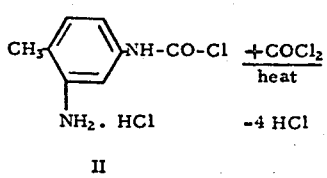

II

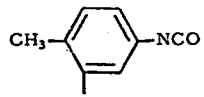

III the diamine (I) initially reacts in the pre-phosgenation stage to form a fine suspension which is believed to be the hydrochloride of the carbamic acid chloride (II), although it can be assumed that bis-hydrochloride (IV) or bis-carbamic acid chloride (V), both of which are also solid substances, are formed at the same time:

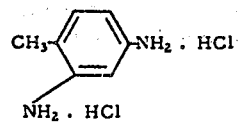

IV

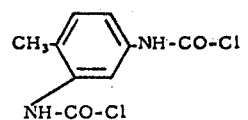

V

In the hot-phosgenation stage, the compounds (II), (IV) and (V) are subsequently reacted with phosgene, which is generally used in excess, to form tolylene-2,4-diisocyanate (III). In either case, therefore, two separate operations are required to produce isocyanates where this procedure is adopted.

Accordingly, there have been many attempts to circumvent or, as it were, to eliminate the cold-phosgenation stage. In one known process, British Pat. Specification No. 901,377, pre-phosgenation is carried out in a self-contained, countercurrent mixing chamber and the suspension formed is delivered directly to the hot-phosgenation stage. A countercurrent mixing chamber of this kind does not have any movable parts, nor does it have a delivery or feed capability. The components are admixed solely by a suitable geomatric arrangement of the mixing chamber in conjunction with the initial pressure under which the amine solution and the phosgene or phosgene solution are delivered into the mixing zone. Unfortunately, this method of carrying out the pre-phosgenation of amines is always disadvantageous when the pre-phosgenation products tend to form insoluble or relatively high molecular weight reaction products which adhere firmly to the wall of the mixing chamber and which build up into relatively thick layers and thus cause blockages. The mixing chamber then has to be dismantled and cleaned which, apart from disrupting production, is extremely undesirable both on account of the toxicity and high volatility of phosgene and on account of the toxic properties of the amines generally used, because the operator has to take elaborate precautionary measures, for instance, when opening flange joints that have been under pressure. Another disadvantage of using a countercurrent mixing chamber as described above lies in its limited scope of application for mixing liquids because the quantities of the components to be mixed have to be in a definite ratio to one another which ratio cannot be varied to any appreciable extent without departing from the optimum range for effective admixture. Since liquids are incompressible, the supply of energy needed to generate relatively intense turbulence and to give adequate admixture, even where the quantitative ratios between the reagents are unfavorable, is only possible to a limited extent. If solid products are formed when the liquid components are combined, it is necessary, in any event, to adhere to certain quantitative ratios determined by the design and construction of the corresponding countercurrent mixing chamber. The amines whose pre-phosgenation by way of a mixing chamber may readily be accompanied by blockages, include, in particular, polyamines such as (I), 4,4'-diaminodiphenyl methane or 1,6-hexamethylene diamine because their bis-hydrochlorides, bis-carbamic acid chlorides or carbamic acid chloride hydrochlorides are substantially insoluble in the solvents used for phosgenation at the pre-phosgenation temperature and because, on account of the polyfunctional character of the aforementioned diamines for example, products of relatively high molecular weight can be formed during pre-phosgenation on account of locally inadequate admixture, as illustrated in the following reaction equation:

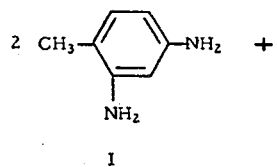

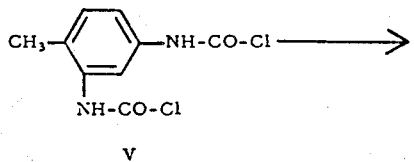

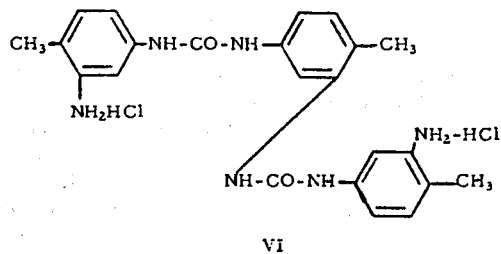

These disadvantages also apply to the use of a countercurrent mixing chamber, for example, for the pre-phosgenation of 2,4-tolylene diamine (I).

In another process for the continuous production of organic isocyanates, a solution of an organic amine is combined with a phosgene solution in turbulent flow in a reactor through which the reaction mixture flows either in a continuous circuit or in continuous loops. Where this procedure is adopted, the danger of blockage at the point of which the amine solution and the phosgene solution are combined is very serious. Here again, there have been many attempts to improve this process.

One of the possible improvements in this process comprises using special mixers for combining the amine solution and the phosgene solution or amine solution and phosgene solution together with recycled isocyanate solution. The actual mixing process takes place in a thin layer, accompanied by high shear stressing of the separately introduced solutions. Blockages are largely avoided by applying shear velocities of at least 700 reciprocal seconds which are achieved by suitable initial pressures under which the reagents are delivered and by suitable design of the mixing system. Unfortunately, this process suffers from the disadvantage that the mixing operation requires relatively large amounts of energy. In addition, due to the severe shear stressing it undergoes, that part of the mixing system in which the actual reaction takes place, being of course a solids-forming reaction accompanied to an extent by the evolution of gases, has to be made of extremely high-grade erosion-proof material in order to assure the mixing system an adequate service life and to utilize the advantages of the process. Another disadvantage of mixing systems of this kind is that they will only take a limited amount of stressing, as illustrated by the fact that inlet openings for the radial or tangential supply of liquid, adjustable independently of one another, are specifically mentioned.

Another method of carrying out the first reaction of an organic amine or of an amine solution with phosgene or with a phosgene solution in the production of isocyanates in such a way that no blockages occur, comprises carrying out the mixing operation in a Venturi mixer into which the reagents have to be introduced under high pressure so that a flow rate high enough to prevent blockages prevails in the reaction zone. This process is attended by the same disadvantages as the other known processes discussed above, such as disproportionately high energy consumption, limited capacity range, because it can only effectively be carried out where the reagents are introduced in certain quantitative ratios, and the need to make those parts of the apparatus which are particularly endangered by the high flow rates at which it is possible to avoid blockages, from expensive special-duty materials.

In another known process, the reaction of an organic amine with phosgene in an inert solvent in the production of isocyanates is carried out continuously in a tubular reactor. In this case, the reagents are mixed together under high pressure. To prevent the components from being re-admixed, which could result in blockages, the tubular reactor has to be designed in such a way that a flow which can be characterized by a Reynolds' number of at least 2100, and preferably from 5000 to 2,000,000 or higher, prevails in the reactor. The generation of flow rates as high as these involves a relatively high energy requirement. Another disadvantage is that the tubular reactors only function optimally in a certain temperature range. Capacity and the question of materials present further problems.

Reference is also made to a process for the production of organic polyisocyanates in which a solution of an organic amine is treated with hydrogen chloride or with a mixture of hydrogen chloride and phosgene in a thin-layer reactor, the reaction mixture formed, consisting predominantly of amine hydrochloride, flowing into a following phosgenation apparatus. One disadvantage of this process is that part or even all of the heat of reaction is dissipated by a cooling medium which flows through a jacket arranged around the thin-layer reactor. The quantity of heat dissipated is lost and cannot be utilized in the following phosgenation apparatus. Another disadvantage is that the amine hydrochlorides formed are precipitated in solid, crystalline form and, hence, give rise to considerable erosion in the reaction zone of the thin-layer reactor.

The cold-phosgenation or pre-phosgenation stage has also been carried out continuously and very quickly by a process in which a solution or suspension of the amine in an inert solvent is continuously combined with intensive stirring in a mixer, which can either be a turbomixer or a rotary pump, in the absence of external cooling and the resulting reaction mixture is subjected to hot-phosgenation in the usual way. The advantages of this particular process are that the components are combined with one another in the absence of cooling, which not only simplifies the process but also saves considerable energy, and that, by virtue of the very fine distribution of the pre-phosgenation products attributable to intensive mechanical admixture of the reactants, hot phosgenation can be carried out more quickly than is possible in conventional two-stage processes, without any disadvantages in regard to the purity and yield of the end products. By virtue of the advantages which they afford, it has been possible to successfully use turbomixers for carrying out pre-phosgenation reactions although they do not by any means represent the optimum in terms of energy. In these turbomixers, the reagents are thoroughly admixed by mechanical means. The reaction mixture is delivered into the turbomixer by the initial pressure under which the components are introduced. Unfortunately, it has not been possible to successfully introduce rotary pumps into whose suction pipe sockets the reagents are continuously introduced through separate pipes, although they combine with the mixing effect the further advantage that they are also able to undertake delivery of the reaction mixture into the following hot-phosgenation stage, which is favorable in terms of energy. The reason for this failure is that it is impossible to prevent insoluble products from settling at that point at which the amine or the amine solution or amine suspension and the phosgene or phosgene solution are combined through separate pipes in the suction pipe sockets, resulting in blockage after a more or less long period of operation, which gives rise to the same operational difficulties as those discussed above with reference to the countercurrent mixing chambers.

Whereas monofunctional amines such as, for example, aniline, α-naphthyl amine, stearyl amine, phenetidine or cyclohexyl amine, whose pre-phosgenation products involve little or no danger of blockage, can be phosgenated in the manner described to form the corresponding isocyanates, it is not possible economically to pre-phosgenate polyfunctional amines such as, for example, tolylene diamine, 4,4'-diaminodiphenyl methane or 1,6-hexamethylene diamine, over a prolonged period by means of a rotary pump, since with polyfunctional amines, after only about 5 to at most about 20 hours, the suction pipe socket of the pump is blocked to such an extent that even rinsing with hot solvent is unable to remedy the situation, with the result that the pump and, in most cases, also the feed and discharge lines have to be dismantled and cleaned. However, since it is those very polyisocyanates which are derived from polyfunctional amines, such as tolylene diisocyanate, 4,4'-diisocyanato diphenyl methane or 1,6-hexamethylene diisocyanate, which commercially are very important products, there is a need to eliminate the deficiencies of the conventional pre-phosgenation techniques referred to without in any way affecting their advantages, such as the relatively short hot-phosgenation time, limited energy consumption and high yield.

It is therefore an object of this invention to provide an improved process for the continuous pre-phosgenation of organic primary amines. It is another object of this invention to provide an improved pre-phosgenation process which minimizes blockages due to deposition of solid material in the process apparatus. The foregoing objects and others which will become apparent from the following description are accomplished in accordance with the invention, generally speaking, by a process comprising combining solutions in inert solvents of an organic primary amine with phosgene, in the absence of external cooling, in the suction side of a multiple-stage rotary pump at high turbulence without any need for adjustment to pressure or flow conditions. The resulting reaction mixture is then subjected to hot phosgenation in the conventional manner. It was found in the course of further development that, where pre-phosgenation is carried out by way of a rotary pump, there is no longer any danger of blockage, even in the event of prolonged periods of operation, providing a multiple-stage rotary pump is used and the phosgene solution is introduced into the multiple-stage rotary pump through the suction pipe inlet and the amine solution is introduced through lateral access point into the suction part of the second stage. To carry out the process according to the invention, conventional multiple-stage rotary pumps must first be modified so as to be provided with a lateral pipe inlet. The point at which the additional inlet is arranged is of crucial importance. This point must lie exactly between the roters of the first and second stages where the turbulence generated by the first impeller is still present in the phosgene solution which has entered through the suction pipe inlet but where the suction effect of the second stage is also effective. The amine solution entering through the lateral access point meets a phosgene solution in a state of high turbulence in the suction part of the second stage. It is also possible to introduce the amine solution into the interior of the multiple-stage rotary pump through several additionally provided lateral sockets, although this procedure does not afford any advantages on account of the problem of uniformly distributing the amine solution. Due to the reaction, the pre-phosgenation products are formed in very fine distribution by virtue of the intensive, mechanically generated turbulence, they are then sucked in by the second stage, further size-reduced and are delivered into the hot-phosgenation zone either as such or optionally after further processing.

Combining the reagents, phosgene solution and amine solution, in the suction part of the first stage in which the phosgene solution is introduced into the suction part of the first stage through the suction pipe inlet of the pump and the base solution through an additional lateral access point, does not have the required effect because the pre-phosgenation products accumulate in compact form due to inadequate turbulence in the suction part of the first stage and, after only a very short period of operation, result in blockages especially where polyfunctional amines are used. If the additional lateral pipe inlet is arranged more towards the first impeller rather than exactly in the middle in the space between the first impeller and the second impeller, phosgene solution can quite easily be forced into the lateral inlet through which the base solution is intended to be delivered into the pump, with the result that the phosgenation products are deposited in and eventually block this inlet. The same occurs when the additional lateral pipe inlet opens directly on to a rotor. If, by contrast, the lateral access inlet for the amine solution is arranged more towards the second impeller in the space between the first impeller and the second impeller, the phosgenation products have no opportunity to be distributed finely enough before they are sucked in by the second stage, with the result that once again blockages can occur. The foregoing observations and experiences regarding the optimum position of the additional lateral access inlet for the amine solution also apply logically as regards the spaces between the second impeller and the third impeller, between the third rotor and the fourth rotor, etc. It is also possible, however, to add the amine solution to the phosgene solution through a lateral pipe inlet situated exactly in the middle of the space between the second impeller and the third impeller or between the third impeller and a fourth impeller, and at a point midway between the first rotor and the second rotor. However, on account of the relatively high pressure which the phosgene solution has at this point it can flow back into the lateral amine inlet after a more or less brief period, resulting in blockage, this procedure is far from reliable in operation. In order to obviate these difficulties, the amine solution has to be delivered into the pump under a definite, elevated pressure which corresponds exactly to that of the phosgene solution at the point at which the amine solution and the phosgene solution are to be combined with one another. Not only does this involve considerable outlay, it also has the disadvantage that, even in the event of very slight fluctuations in pressure, blockage can again occur. Combining the phosgene solution and the amine solution in the suction part of the second stage by the process according to the invention has the advantage over this procedure in that the pressures under which the phosgene solution and amine solution are delivered into the pre-phosgenation mixing pump do not have to be precisely coordinated with one another, but instead merely have to be of the same order. As a result, the mixed phosgenation process according to the invention using a multiple-stage rotary pump has a wide range of variation in regard also to the quantitative ratio between the reaction components. The scope of application can additionally be increased by using a multiple-stage rotary pump which is able to deliver a larger volume than that which corresponds to the sum total of the phosgene solution and the amine solution. Unlike a countercurrent mixing chamber, a tubular reactor, a Venturi mixer or any other similar mixing system, in which high rates of flow are necessary, the turbulence required to obtain optimum admixture of the reagents is still safely present in the multiple-stage rotary pump operated in the under-loaded range. This means that multiple-stage rotary pumps of this kind will take loads within very wide limits without being deprived in any way of their effectiveness in performing the required function of mixing the reaction components and delivering the reaction mixture, even over prolonged periods of operation.

Figure 2:
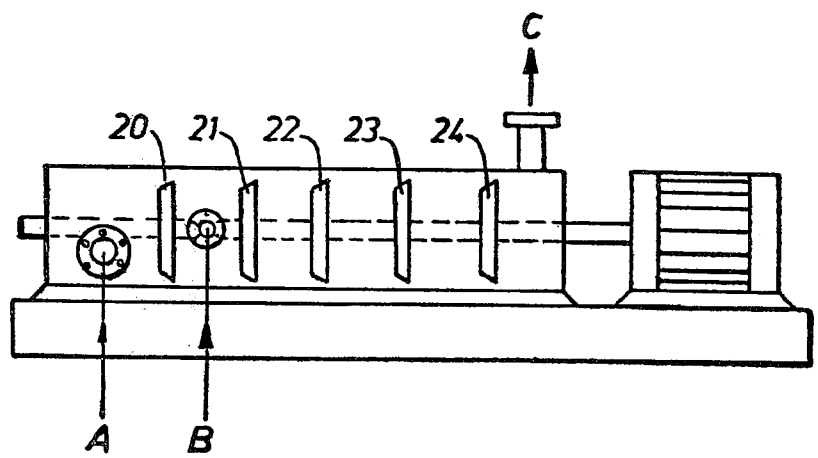

Two embodiments of the invention are diagrammatically illustrated by way of example in the accompanying drawing and discussed in more detail in the following. In the accompanying drawing:

FIG. 1 represents a two-stage rotary pump.
FIG. 2 represents a five-stage rotary pump.

In FIG. 1, phosgene solution A is introduced before the first rotor 10. The amine solution B is introduced between the first rotor 10 and the second rotor 11. The pre-phosgenation mixture C is discharged into a hot phosgenation stage after leaving the rotary pump.

In FIG. 2, phosgene solution A is introduced before the first rotor 20. Once again, the amine solution B is introduced between the first rotor 20 and the second rotor 21. The rotors 22, 23 and 24 are provided to intensify admixture. The pre-phosgenation mixture C is discharged to a hot-phosgenation stage after leaving the rotary pump.

In principle, any conventional two-stage to six-stage pump can be used for carrying out the pre-phosgenation according to the invention provided that they do not operate by self-induction and have a design which enables the installation of the lateral inlet for adding the amine solution such that it is arranged midway between the first impeller and the second impeller. It is of advantage to use pumps of the kind which, internally, have sufficiently wide passages so that even a suspension of solid particles in a liquid can be satisfactorily delivered. Two-stage to six-stage rotary pumps, of the kind illustrated in, for example, Pamphlet No. S-4400-12 issued by Pumpenfabrik Ritz and Schweizer, Schwabisch Gmund, have proved to be particularly suitable. The impellers advantageously rotate at speeds of from 1000 to 3000 revolutions per minute. It is best to introduce the reagents, phosgene and amine solutions, into the pump in the form of a solution in an inert solvent suitable for phosgenation reactions.

Aromatic and aliphatic (chlorinated) hydrocarbons are particularly suitable solvents, some examples of which are carbon tetrachloride, dichloroethane, benzene, toluene, xylene, chlorobenzene, dichlorobenzenes, dichlorotoluenes, trichlorobenzenes, petroleum fractions or chlorinated diphenyls. It is also possible, however, to use such solvents as ethyl acetate, 1,4-dioxan, tetramethylene sulphone, dimethyl sulphone or benzonitrile, and mixtures thereof. It is preferred, however, to use chlorobenzene and o-dichlorobenzene which are commonly used for phosgenation reactions. However, the pre-phosgenation process according to the invention is not confined to any one solvent.

The reaction components, phosgene solution and amine solution, can be combined with one another in the absence of cooling in the suction part of the second stage of a two- to six-stage rotary pump, which not only greatly simplifies the process, but also saves considerable energy. The concentrations and quantities of both solutions can be varied within wide limits, with the proviso that the quantity of phosgene should always be adequate for the purposes of the reaction. The phosgene solution is best used in excess. An approximately 5% to 40% by weight amine solution and an approximately 20% to 65% by weight phosgene solution are generally used. The quantity of phosgene should be such that there is at least 1 mol of phosgene per gram equivalent of amine. It is preferred to use from about 1.5 to about 3 mols of phosgene per mol of amine. However, the pre-phosgenation process according to the invention is by no means confined to definite concentrations in the amine solution or phosgene solution or to a certain excess of phosgene as such details are well-known to the art.

Due to the heat of reaction, admixture of the phosgene solution and amine solution is accompanied by a rise in temperature, although this is by no means critical to the pre-phosgenation process according to the invention in its practical application. The temperature at which the pre-phosgenation mixture leaves the multiple-stage rotary pump may be in the range of from about 50°C. to about 100°C. without any adverse effect either upon the yield or upon the purity of the end products. In contrast to pre-phosgenation carried out by the conventional two-stage process, there is no need for the phosgene solution or the amine solution to be cooled at all before entry into the pre-phosgenation mixing pump. The phosgene solution and the amine solution are preferably used at the temperatures which they assume in any case in operation, i.e., in the range of from about −10°C. to about 250°C. for the phosgene solution and from about 50°C. to about 110°C. for the amine solution. The pre-phosgenation products are then discharged by the rotary pump to a hotphosgenation stage where the reaction hot-phosgenation the required isocyanate is completed, optionally accompanied by the introduction of more phosgene. By virtue of the extremely fine distribution of the pre-phosgenation products, the reaction takes place more quickly and is accompanied by fewer secondary reactions than in conventional processes, and leads to an increased yield of isocyanate. There is no need to use special-duty materials for the manufacture of suitable pumps. After they have been modified to accommodate the lateral inlet for the amine solution, conventional two-stage rotary pumps of, for example, grey cast iron can be used in continuous operation.

The hot phosgenation stage following the pre-phosgenation process according to the invention may be carried out by any one of the known methods and does not have any direct bearing upon the pre-phosgenation process according to the invention. The hot-phosgenation stage may be carried out in the presence or absence of additional phosgene or solution of phosgene under elevated pressure, under a slight excess pressure or at normal pressure either continuously or on the batch principle. To insure that the advantages of the process according to the invention are left fully intact, the hot phosgenation stage should preferably be carried out as near continuously as possible either in vessels or in towers at normal pressure or at a slight excess pressure of up to about 1.5 atmospheres. It is of particular advantage to allow the pre-phosgenation mixture leaving the rotary pump to flow continuously upwards or downwards into a heatable vessel or tower and to complete the reaction by the supply of heat. It is also possible to arrange several vessels or towers one behind the other or to use combinations of vessels and towers where it is desired to adhere to a certain temperature range in order to optimize control of the reaction in the hot-phosgenation stage.

The pre-phosgenation process according to the invention is applicable to any monofunctional or polyfunctional aliphatic, cycloaliphatic, araliphatic or aromatic amines.

Some examples of suitable amines are methyl amine, propyl amine, cetyl amine, stearyl amine, hexamethylene diamine, butane diol-1,4-bis-γ-aminopropyl ether, cyclohexyl amine, 1,4-bis-aminomethyl cyclohexane, 4-aminobenzyl amine, aniline, o-, m-, p-chloro aniline, 3,4-dichloroaniline, anisidine, o-, m-, p-nitroaniline, m-, p-xylylene diamine, m-, p-phenylene diamine, 1-amino-3,3,5-trimethyl-5-aminomethylcyclohexane, 2,4-, 2,6-tolylene diamine, 4,4'-diamino diphenyl methane, 2,4'-diamino diphenyl methane, thiophosphoric acid-4,4',4''-triaminotriphenyl ester and the like. It is emphasized however, that the continuous pre-phosgenation process according to the invention is always used in preference to conventional process for the continuous pre-phosgenation of polyfunctional amines which, in many cases, can only be carried out under considerable difficulty, more particularly for the continuous pre-phosgenation of 2,4-tolylene diamine, 2,6-tolylene diamine or mixtures of 2,4- and 2,6-tolylene diamine, 4,4'-diamino diphenyl methane and the isomer mixtures obtained by condensing aniline with formaldehyde or 1,6-hexamethylene diamine.

The invention is further illustrated in the following examples wherein all parts and percentages are by weight unless otherwise indicated.

EXAMPLES

EXAMPLE 1

In the production of tolylene diisocyanate on an industrial scale, pre-phosgenation of the freshly distilled tolylene diamine used (composition approximately 1% to 4% of 2,3-tolylene diamine and 3,4-tolylene diamine, approximately 78% to 82% of 2,4-tolylene diamine and approximately 17% to 22% of 2,6-tolylene diamine) is carried out as follows: About 2,200 liters per hour of a 40% phosgene solution in chlorobenzene are introduced into the suction inlet of a five-stage rotary pump of the non-self-induction type whose delivery for water is quoted as being 100 cubic meters per hour over a height in access of 100 meters, while about 1,166 liters per hour of tolylene diamine solution, produced by dissolving about 230 kg of tolylene diamine in 1,155 kg of chlorobenzene, are introduced into the suction part of the second pump stage through an additional laterally arranged inlet as illustrated in FIG. 2. The phosgene solution is mixed and reacted with the tolylene diamine solution in the suction part of the second pump stage, the admixture and reaction cycle continues without interruption for a period of about 400 hours. The reaction mixture formed (suspension of the pre-phosgenation products in chlorobenzene) is pumped continuously at a temperature of about 65°C. from the five-stage rotary pump into a hot-phosgenation stage and worked up into tolylene diisocyanate. The yield the about 6% of theoretical higher than in he conventional two-stage process for phosgenating the same tolylene diamine.

EXAMPLE 2

The range of variation of the pre-phosgenation stage is investigated in a second large-scale test. The solution of phosgene in chlorobenzene introduced through the suction pipe inlet of a two-stage rotary pump of the non-self-induction type whose delivery for water is quoted at 100 cubic meters per hour over a height of 56 meters, is varied between 2000 kg)hr in quantity and between 40% and 50% by weight in concentration. The solution of tolylene diamine in chlorobenzene, of the same quality as in Example 1, introduced into the suction part of the second stage of the rotary pump through an additional laterally arranged inlet (see FIG. 1) is varied between 850 kg/hr and 1,700 kg/hr in quantity and between 16% and 25% by weight in concentration. The eaction mixture is pumped from the two-stage rotary pump into a following hot-phosgenation stage at a temperature of from 65° to about 80°C. continuously without interruption over a period of about 1,270 hours and worked up into tolylene diisocyanate. The yield obtained was increased by 5% of the theoretical in comparison with the conventional two-stage process. The quantities of phosgene solution and amine solution used and the periods of operation are set out in the following Table:

| Duration | kg/hr of Phosgene Solution | % | Base Solution | | |
|---|---|---|---|---|---|
| | | | kg/hr of Tolylene Diamine | kg/hr of Chlorobenzene | % |
| 8 Days | 2,810 | 40 | 208 | 1,120 | 15.7 |
| 4 Days | 2,000 | 40 | 150 | 700 | 17.7 |
| 2 Days | 2,740 | 45 | 260 | 1,300 | 16.7 |
| 3 Days | 3,300 | 50 | 350 | 1,050 | 25.0 |
| 5 Days | 2,730 | 45 | 275 | 1,170 | 19.0 |
| 4 Days | 3,940 | 40 | 327 | 1,450 | 18.5 |
| 6 Days | 3,020 | 50 | 327 | 1,450 | 18.5 |
| 2 Days | 2,515 | 45 | 260 | 1,300 | 16.7 |
| 7 Days | 2,730 | 45 | 275 | 1,170 | 19.0 |
| 3 Days | 2,515 | 45 | 260 | 1,300 | 16.7 |
| 4 Days | 3,020 | 50 | 327 | 1,350 | 19.5 |
| 5 Days | 2,015 | 50 | 222 | 900 | 19.8 |

After the first part of the large-scale test had been completed, the same two-stage rotary pump was connected by lines to another hot-phosgenation apparatus consisting of two heatable steel towers 1 meter in diameter and 9 meters long arranged one behind the other. Once again, tolylene diamine of the same quality as in Example 1, dissolved in o-dichlorobenzene, was reacted with phosgene in the manner described. In long-term operation, the following quantities were reacted with one another: through the suction pipe inlet, an average of 16,700 kg/hr of a 40% phosgene solution in o-dichlorobenzene and, through the lateral inlet, an average of 8,000 kg/hr of a 25% tolylene diamine solution in o-dichlorobenzene. The reaction mixture was pumped continuously without interruption from the two-stage rotary pump into the tower cascade at a temperature of 84° to 89°C. The yield obtained was increased by 4% of theoretical in comparison with the conventional two-stage process.

EXAMPLE 3

About 2,230 kg/hr of a 50% phosgene solution in chlorobenzene are introduced through the suction pipe inlet of a two-stage rotary pump of the non-self-induction type whose delivery for water is quoted at 100 cubic meters per hour over a height of 56 meters, while a solution of 500 kg/hr of p-chloroaniline in 885 kg of chlorobenzene is introduced into the suction part of the second stage through an additional, laterally arranged inlet (FIG. 1). The reaction mixture is pumped from the two-stage rotary pump into a following hot-phosgenation stage continuously without interruption over a period of about 365 hours at a temperature of from about 60°C. to about 65°C., and worked up into p-chlorophenyl isocyanate. The yield of p-chlorphenyl isocyanate obtained is higher by 4% of theoretical than the yield obtained where the p-chloroaniline is pre-phosgenated in a countercurrent mixing chamber.

EXAMPLE 4

3,360 Kg/hr of a 45% solution of phosgene in chlorobenzene, are introduced through the suction inlet of a two-stage rotary pump of the non-self-induction type with a delivery for water of 100 cubic meters per hour over a height of 56 meters, while a solution of 600 kg/hr of a condensation product of aniline and formaldehyde of which approximately 60% consists of polyamines, is introduced into the suction part of the second stage through an additional laterally arranged inlet (FIG. 1). The reaction mixture was pumped continuously without interruption from the two-stage rotary pump into a following hot-phosgenation stage at a temperature of about 65°C. to about 70°C., and worked up into polymeric isocyanate. The hot-phosgenation reaction required only two thirds of the residence time required to complete isocyanate formation after pre-phosgenation in a countercurrent mixing chamber.

It is to be understood that any of the components and conditions mentioned as suitable herein can be substituted for its counterpart in the foregoing examples and that although the invention has been described in considerable detail in the foregoing, such detail is solely for the purpose of illustration. Variations can be made in the invention by those skilled in the art without departing from the spirit and scope of the invention except as is set forth in the claims.

What is claimed is:

1. A process for the continuous pre-phosgenation of organic primary amines which minimizes blockages due to deposition of solid material in the process apparatus comprising mixing, in the absence of external cooling, in the suction side of a multi-stage rotary pump of the non-self-induction type, a 20 to 65% by weight solution in an inert organic solvent of phosgene and a 5–40% by weight solution in an inert organic solvent of an organic primary amine, from about 1.5 to about 3 mols of phosgene being present per gram equivalent of said amine the phosgene solution being introduced via the suction inlet of the pump, and the amine solution being introduced via a lateral access inlet situated midway between the first and second impeller of the pump, the pre-phosgenation mixture thus obtained being conveyed via the discharge outlet of the pump to a hot-phosgenation stage.

2. The process of claim 1 wherein the organic primary amine is a primary aromatic monoamine.

3. The process of claim 1 wherein the organic primary amine is a polyprimary organic polyamine.

4. The process of claim 3 wherein the polyamine is selected from the group consisting of 2,4-tolylene diamine, 2,6-tolylene diamine, 4,4'-diaminodiphenyl methane, 1,6-hexamethylene diamine and polyphenyl polymethylene polyamines produced by condensing aniline with formaldehyde.

5. The process of claim 1 wherein the inert organic solvent is chlorobenzene or o-dichlorobenzene.

\* \* \* \* \*